(12) United States Patent
Yung

(10) Patent No.: US 7,662,582 B2
(45) Date of Patent: *Feb. 16, 2010

(54) METHOD OF IDENTIFYING CANCER BIOMARKERS AND CANCER PROGRESSION

(75) Inventor: Benjamin Yat Ming Yung, Tao-Yuan (TW)

(73) Assignee: Chang Gung University, Tao-Yuan (TW)

( * ) Notice: Subject to any disclaimer, the term of this patent is extended or adjusted under 35 U.S.C. 154(b) by 190 days.

This patent is subject to a terminal disclaimer.

(21) Appl. No.: 11/767,511

(22) Filed: Jun. 24, 2007

(65) Prior Publication Data

US 2008/0318263 A1  Dec. 25, 2008

(51) Int. Cl.
*C12Q 1/37* (2006.01)
*C12N 9/72* (2006.01)
(52) U.S. Cl. .......................... 435/23; 435/215
(58) Field of Classification Search .................. None
See application file for complete search history.

(56) References Cited

OTHER PUBLICATIONS

Hasui et al. The Content of Urokinase-Type Plasminogen Activator and Tumor Recurrence in Superficial Bladder Cancer; The Journal of Urology, vol. 151 (1994) pp. 16-20.*
Nielsen, L.S., et al. Enzyme-Linked Immunosorbent Assay for Human Urokinase-Type Plasminogen Activation and its Proenzyme Using a Combination of Monoclonal and Polyclonal Antibodies; Journal of Immunoassay, vol. 7, No. 3 (1986) pp. 209-228.*
Kielberg et al. Proenzyme to Urokinase-Type Plasminogen Activator in the Mouse in Vivo; FEBS Letters, vol. 182, No. 2 (1985) pp. 441-445.*
Chiao-Yun Lin, et al, Searching Cell-secreted proteomes for potential urinary bladder tumor markers, Wiley Interscience, www.interscience.wiley.com, vol. 6 Issue 15, Jul. 3, 2006.

* cited by examiner

*Primary Examiner*—Rebecca E. Prouty
*Assistant Examiner*—Paul C. Martin
(74) *Attorney, Agent, or Firm*—Ming Chow; Sinorica, LLC

(57) ABSTRACT

An efficient method for identifying important cancer biomarkers and identifying progression of bladder cancer using pro-u-PA as a clinical tool is provided. Searching for biomarkers critical for bladder carcinoma diagnosis and prognosis, secreted proteomes of highly malignant U1 and pre-malignant U4 cell lines are first analyzed. Proteins in the cultured media of the U1 and U4 cell-lines were systematically examined by SDS-PAGE combined with MALDI-TOF mass spectrometry. Expression of pro-u-plasminogen activator (pro-u-PA) was confirmed by Western blot analysis and further evaluated. A statistically significant relationship between the low level and absence of pro-u-PA in urine with high stages and grades of the tumor samples was established. Constitutive expression of Ras dominant negative protein led to increased expression of pro-u-PA in cultured media, indicating the loss of pro-u-PA is associated with oncogenic transformation. The loss of pro-u-PA in urine has been identified as a marker of more advanced bladder carcinoma.

7 Claims, 9 Drawing Sheets

| Protein identified | $M_r$ | pI | Band number[a] (Score[b]/Seq Cov[c]) | |
|---|---|---|---|---|
| | | | MGH-U1 | MGH-U4 |
| Laminin alpha-5 chain | 411712 | 6.61 | 60 (63/10%) | |
| Fibronectin precursor | 260125 | 5.45 | 61 (136/19%) | 1 (121/21%) |
| ADP-ribosylation factor guanine nucleotide-exchange factor2 | 204517 | 6.07 | 62 (77/13%) | |
| Complement component 3 precursor | 188612 | 6.02 | 64 (114/21%) | 2 (114/21%) |
| Alpha3b subunit of laminin 5 | 149943 | 6.32 | | 3 (65/19%) |
| Protein tyrosine phosphatase | 211738 | 6.03 | 65 (183/29%) | 4 (183/29%) |
| Laminin B1K chain precursor | 133278 | 7.3 | 67 (68/21%) | 5 (68/21%) |
| Calsyntenin-1 precursor | 111000 | 4.81 | 68-69 (74/25%) | 6 (72/23%) |
| VCL protein | 117243 | 5.83 | 69 (62/21%) | 7 (62/21%) |
| KIAA0088 | 107166 | 5.71 | 71 (108/38%) | 9 (108/38%) |
| Glucosidase II | 107297 | 5.71 | 71 (108/37%) | 9 (108/37%) |
| actinin, alpha 1 | 103573 | 5.25 | 73 (70/31%) | 10 (66/29%) |
| actinin, alpha 4 | 105253 | 5.27 | 74 (66/29%) | 11-14 (75/20%) |
| amyloid beta A4 protein precursor isoform a | 87932 | 4.73 | 75 (67/25%) | 12-14 (67/25%) |
| quiescin Q6 | 83338 | 9.13 | 76 (76/25%) | 12-14 (76/25%) |
| heat shock 90kDa protein | 83560 | 4.97 | 77 (104/41%) | 15 (104/41%) |
| procollagen-lysine, 2-oxoglutarate 5-dioxygenase 3 | 85312 | 5.69 | 78 (62/22%) | 16 (62/22%) |
| heat shock 70kDa protein 5 | 72404 | 5.07 | 80 (133/50%) | 18 (113/41%) |
| matrix metalloproteinase 2 | 74937 | 5.26 | 81 (92/25%) | 19 (92/25%) |
| heat shock 70kDa protein 8 | 71086 | 5.37 | 82-84 (75/28%) | 20-22 (108/48%) |
| cytokeratin 9 | 62324 | 5.19 | 85 (95/44%) | 23 (95/44%) |
| BIGH3 | 56949 | 6.97 | 86 (69/27%) | 24 (69/27%) |
| moesin/anaplastic lymphoma kinase fusion protein | 62007 | 7.61 | 87 (65/37%) | 25 (65/37%) |
| M2-type pyruvate kinase | 58447 | 7.95 | 87 (65/36%) | 25 (65/36%) |
| thioredoxin reductase | 55266 | 6.07 | 88 (68/34%) | 26-27 (68/34%) |
| KM-102-derived reductase-like factor | 60986 | 6.27 | 89 (68/34%) | 28 (68/33%) |
| keratin 10; cytokeratin 10 | 59024 | 5.09 | 90 (132/34%) | 29 (132/34%) |
| glucose-6-phosphate dehydrogenase | 55195 | 6.91 | 90 (76/34%) | 29 (76/34%) |
| tubulin, beta, 2 | 50263 | 4.79 | 91 (121/46%) | 30 (96/41%) |
| Urokinase plasminogen activator precursor | 47722 | 8.69 | 92 (111/54%) | 32 (114/57%) |
| plasminogen activator inhibitor 1 | 45103 | 6.68 | 93-95 (181/62%) | 33-35 (97/41%) |
| beta actin | 41326 | 5.56 | 95-96 (78/35%) | 36-37 (107/39%) |
| isocitrate dehydrogenase beta chain isoform B | 42702 | 8.64 | 97 (63/27%) | 38 (63/27%) |
| aldolase A | 39728 | 8.39 | 98 (75/48%) | 39 (75/48%) |
| 3alpha-hydroxysteroid dehydrogenase | 37226 | 7.60 | 100 (62/34%) | 42 (62/34%) |
| Aldo-keto reductase family 1 member C3 | 37227 | 8.05 | 100 (61/34%) | 42 (61/34%) |
| glyceraldehyde-3-phosphate dehydrogenase | 36205 | 8.26 | 101 (60/34%) | |
| Annexin A2 | 38826 | 7.57 | 102,104-105 (68/41%) | 43,45-46 (66/29%) |
| stanniocalcin 2 | 34083 | 6.93 | 106-107 (65/43%) | 47 (65/43%) |
| phosphoglycerate mutase 1 | 28902 | 6.67 | 109 (57/47%) | 48 (57/47%) |
| Triosephosphate Isomerase | 26812 | 6.51 | 110-111 (127/85%) | 49-50 (83/53%) |
| glutathione S-transferase | 23595 | 5.43 | 112 (72/59%) | 51 (72/59%) |
| lipocalin 2 | 22745 | 9.02 | 112 (90/64%) | 51 (90/64%) |
| tissue inhibitor of metalloproteinase 1 precursor | 23840 | 8.64 | 113 (82/63%) | 52 (87/79%) |
| cyclophilin | 18232 | 7.68 | 114 (70/41%) | 53 (65/35%) |
| nucleoside-diphosphate kinase 1 isoform a | 19873 | 5.42 | 115 (60/47%) | 54 (60/47%) |
| Peptidylprolyl isomerase A | 18233 | 7.68 | 116 (91/63%) | 55 (91/63%) |
| cystatin SN precursor | 16609 | 6.73 | 118 (71/56%) | 56 (71/56%) |
| protein SAP1 | 13495 | 4.67 | 119 (58/55%) | 57 (58/55%) |
| Chain M, Human Class I Histocompatibility Antigen A2 | 11592 | 6.46 | 120 (61/76%) | 58 (61/76%) | a) Numbering of the protein bands detected in Fig. 1A.
b) The Mascot search score of identified proteins is shown.
c) The percentage of sequence coverage (Seq Cov) of matched peptides in the protein identified is shown.

Figure 1C

| Protein identified | Cancer type | Reference |
| --- | --- | --- |
| Laminin alpha-5 chain | Non-small cell lung cancer | 1 |
| | Prostate cancer | 2 |
| Protein tyrosine phosphatase | Breast cancer | 3 |
| | Gastric carcinoma | 4 |
| Heat shock protein 90 | Gastric carcinoma | 5 |
| | Bladder cancer | 6 |
| Matrix metalloproteinase-2 | Non-small cell lung cancer | 7 |
| | Oral carcinoma | 8 |
| | Breast cancer | 9 |
| | Colorectal cancer | 10 |
| Thioredoxin reductase | Lung cancer | 11 |
| | Pancreatic cancer | 12 |
| Stanniocalcin 2 | Breast cancer | 13 |
| Cyclophilin A | Hepatocellular carcinoma | 14 |
| | Lung cancer | 15 |
| Annexin A2 | Renal cell carcinoma | 16 |
| | Osteosarcoma | 17 |
| | Gastric carcinoma | 18 |
| Glutathione-S-transferase | Larynx cancer | 19 |
| | Breast cancer | 20 |
| | Prostate cancer | 21 |
| Triosephate isomerase | Lung adenocarcinoma | 22 |
| Lipocalin2 | Pancreatic cancer | 23 |
| | Ovarian carcinoma | 24 |
| Fibronectin | Breast cancer | 25 |
| | Ovarian carcinoma | 26 |
| Heat shock protein 70 | Colonic adenocarcinoma | 27 |
| | Prostate cancer | 28 |
| Plasminogen activator inhibitor 1 | Breast cancer | 29 |
| | Head/neck cancer | 30 |
| | Lung cancer | 31 |
| Aldolase A | Renal cell carcinoma | 32 |
| | Lung cancer | 33 |
| Phosphoglycerate mutase 1 | Breast cancer | 34 |
| | Lung adenocarcinoma | 35 |
| M2 pyruvate kinase | colorectal cancer | 36 |
| | Gastrointestinal cancer | 37 |

Figure 1D

| Cancer patients no. | 17 | 22 | 24 | 26 | 28 | 27 | 16 |
|---|---|---|---|---|---|---|---|
| Stage | T1 | T1 | Ta | Ta | Ta | Ta | T2 |
| Grade | L | L | H | L | L* | H | H |

\* Papillary urothelial neoplasm of low malignant potential

| Groups | Urine level of pro-u-PA | Tumor stage | Tumor grade |
|---|---|---|---|
| Cancer/No. | | | |
| 1 | - | T3 | High grade |
| 2 | - | T2 | High grade |
| 3 | - | T1 | Low grade |
| 4 | - | T1 | High grade |
| 5 | - | T3 | High grade |
| 6 | - | Ta | Low grade |
| 7 | - | T1 | Low grade |
| 8 | - | T1 | High grade |
| 9 | - | T1 | High grade |
| 10 | - | T1 | High grade |
| 11 | - | T3 | High grade |
| 12 | - | T2 | High grade |
| 13 | - | T2 | High grade |
| 14 | - | T3 | High grade |
| 15 | - | T4 | High grade |
| 16 | - | T1 | High grade |
| 17 | + | T1 | Low grade |
| 18 | + | T1 | High grade |
| 19 | + | T2 | High grade |
| 20 | + | T1 | Low grade |
| 21 | + | Ta | PUNLMP* |
| 22 | + | T1 | Low grade |
| 23 | + | Ta | PUNLMP |
| 24 | + | T1 | High grade |
| 25 | + | T1 | High grade |
| 26 | + | T1 | Low grade |
| 27 | + | T1 | High grade |
| 28 | + | Ta | PUNLMP |
| 29 | + | Ta | PUNLMP |
| 30 | + | Ta | PUNLMP |
| 31 | + | T1 | Low grade |
| 32 | + | T1 | Low grade |
| 33 | + | T1 | Low grade |

Non-cancer with

UTI$^{\Psi}$/No.
| | |
|---|---|
| 1 | + |
| 2 | + |
| 3 | + |
| 4 | + |
| 5 | + |
| 6 | + |
| 7 | + |
| 8 | + |

Non-cancer/No.
| | |
|---|---|
| 1 | + |
| 2 | + |
| 3 | + |

Figure 2C

| | |
|---|---|
| 4 | + |
| 5 | + |
| 6 | + |
| 7 | + |
| 8 | + |
| 9 | + |

*Papillary urothelial neoplasm of low malignant potential $^\Psi$Urinary tract infection +, Detectable in urine −, Not detectable in urine

Figure 2C

Identification of proteins down regulated in DN-Ras-U1 cells

| No. | Protein identified | Mr | Score[b]/Seq Cov[c] |
|---|---|---|---|
| 1 | Heat shock protein 70kDa | 72402 | 86/30% |
| 2 | M2-type pyruvate kinase | 58447 | 74/25% |
| 3 | Glyceraldehydes-3-phosphate dehydrogenase | 36201 | 72/37% |
| 4 | Lactate dehydrogenase A | 36950 | 47/62% |

Identification of proteins up regulated in DN-Ras-U1 cells

| No. | Protein identified | Mr | Score[b]/Seq Cov[c] |
|---|---|---|---|
| 5 | Phosphoglycerate kinase 1 | 44985 | 72/31% |
| 6 | Triosephosphate isomerase 1 | 26938 | 136/67% | b) The Mascot search score of identified proteins is shown.
c) The percentage of sequence coverage (Seq Cov) of matched peptides in the protein identified is shown.

Figure 3C

METHOD OF IDENTIFYING CANCER BIOMARKERS AND CANCER PROGRESSION

BACKGROUND OF THE INVENTION

1. Field of the Invention

The present invention relates to cancer detection. More specifically, the present invention discloses an efficient method for identifying important cancer biomarkers and identifying cancer progression using loss of pro-u-PA in urine as a marker of more advanced carcinoma.

2. Description of the Prior Art

Transitional cell carcinoma of the bladder is the second most common malignancy of the genitourinary tract and the second most common cause of death from genitourinary tumors. Depending on the depth of muscle invasion, bladder cancers tend to occur in two principal forms: low-grade superficial tumors and high-grade invasive cancer. Superficial bladder cancer accounts for approximately 70% to 80% of all newly diagnosed bladder cancers. Because of the multifocal nature of urothelial cancers, patients who survive bladder cancer remain at risk of invasive disease. Most invasive tumors are nodular, metastatic during the early phase, and have poor prognosis.

The major problem with bladder cancers is the high recurrence rate of superficial cancers: more than half of superficial tumors recur within 5 years and 10-20% of these progress to invasive disease. It is thus important to detect the early recurrence of superficial cancer before the cells undergo changes that lead to invasive phenotype. Clinical and histo-pathological factors that might assist in the prediction of tumor recurrence and the progression of bladder cancer have been studied. These parameters, when used with the TNM system, will serve as useful and specific tools to provide crucial information about the response to treatment and prognosis of cancer. An ideal prognostic factor must be of sufficient sensitivity and specificity so as to allow treatment decisions on a case-by-case basis. Cytologic analysis of voided urine is the most commonly used noninvasive method for detecting transitional cell carcinoma, but its utility is severely constrained by its low sensitivity. Several potential diagnostic markers for bladder cancer have been identified, including nuclear matrix protein 22, bladder tumor antigen, and telomerase. Although analysis of these markers allows a more sensitive detection of bladder cancer than urine cytology, their use is limited by low specificity.

On the other hand, specific genetic alterations have been implicated in the molecular pathogenesis of transitional cell carcinoma, with mutations reported in the cell cycle regulatory genes, oncogenes, and tumor suppressor genes. However, it has proven difficult to use these genetic alterations as diagnostic markers of bladder cancer because of their low sensitivity.

Therefore there is need for an improved noninvasive method for finding markers of bladder cancer and for efficiently detecting cancer progression.

SUMMARY OF THE INVENTION

To achieve these and other advantages and in order to overcome the disadvantages of the conventional method in accordance with the purpose of the invention as embodied and broadly described herein, the present invention provides an efficient and effective method for detecting the progression of cancer.

An object of the present invention is to provide an improved noninvasive method for finding markers of bladder cancer.

Another object of the present invention is to provide a method for efficiently detecting cancer progression.

Another object of the present invention is to provide a method of identifying cancer progression using loss of pro-u-PA in urine as a marker of more advanced carcinoma.

Malignant progression is a complex and poorly understood process that appears to involve genetic and epigenetic factors. Establishing the profile of proteins secreted from bladder cancer cell lines in cultured-medium is an important step toward identifying molecular markers of carcinogenesis that would form the basis of a test for diagnosis and monitoring prognosis. Proteins secreted by or shed from the tumor cells are, theoretically, more likely than those that reside in tumor cells to be detectable in body fluids such as urine. It is also possible that certain metabolites are secreted and thus are detectable in urine of normal individuals while they are converted and/or absent in urine of cancer patients. In a study conducted according to an embodiment of the present invention, proteins secreted from highly malignant U1 and pre-malignant U4 bladder cell lines were thus first analyzed by sodium dodecyl sulfate-polyacrylamide gel electrophoresis (SDS-PAGE) and matrix-assisted laser desorption/ionization-time of flight (MALDI-TOF) mass spectrometry. Although some potential markers with low expression may be missed, the present invention uses the combination of 1-D gel electrophoresis and MALDI-TOF-MS to efficiently minimize the interference of tumor-host microenvironment, because only proteins secreted by or shed from cells are to be analyzed. 1-D separation strategy followed by MALDI will miss the lower abundant proteins in the band. Hence an additional separation strategy such as 2-D or I-D followed by LC-MS/MS identifies more potential markers. Among the identified proteins, the level of pro-u-plasminogen activator (pro-u-PA) was evaluated and compared by Western blotting in urines from cancer patients and normal controls. The association of urinary pro-u-PA expression with clinical outcome was determined. This is useful as a marker of advanced bladder cancer.

In analyzing urine samples from bladder cancer patients and normal subjects, a statistically significant relationship between the low level and absence of pro-u-PA in urine with high stages and grades of the tumor samples was confirmed. Constitutive expression of Ras dominant negative protein led to increased expression of pro-u-PA in cultured media, indicating the loss of pro-u-PA is associated with oncogenic transformation. Analysis of cancer-secreted proteomes is a feasible, non-invasive and efficient strategy for searching potential bladder tumor biomarkers.

The method of the present invention utilizes the loss of pro-u-PA in urine as marker of more advanced bladder carcinoma. As a result, the present invention provides an effective and non-invasive method of detecting cancer progress.

These and other objectives of the present invention will become obvious to those of ordinary skill in the art after reading the following detailed description of preferred embodiments.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

FIG. 1C is a table illustrating bladder cancer cell line-secreted protein identified by MALDI TOF MS according to an embodiment of the present invention;

FIG. 1D is a table illustrating Bladder cancer cell line-secreted proteins known to be highly-expressed or deregulated in other types of cancer according to an embodiment of the present invention;

FIG. 2C is a table illustrating background and clinical characteristics of 50 cases stratified by urine analysis according to an embodiment of the present invention;

FIG. 3C is a table illustrating differential protein expression profiles of pcDNA3.1-U1 & DN-Ras-U1 cells according to an embodiment of the present invention.

DESCRIPTION OF THE PREFERRED EMBODIMENTS

Figure 1A:
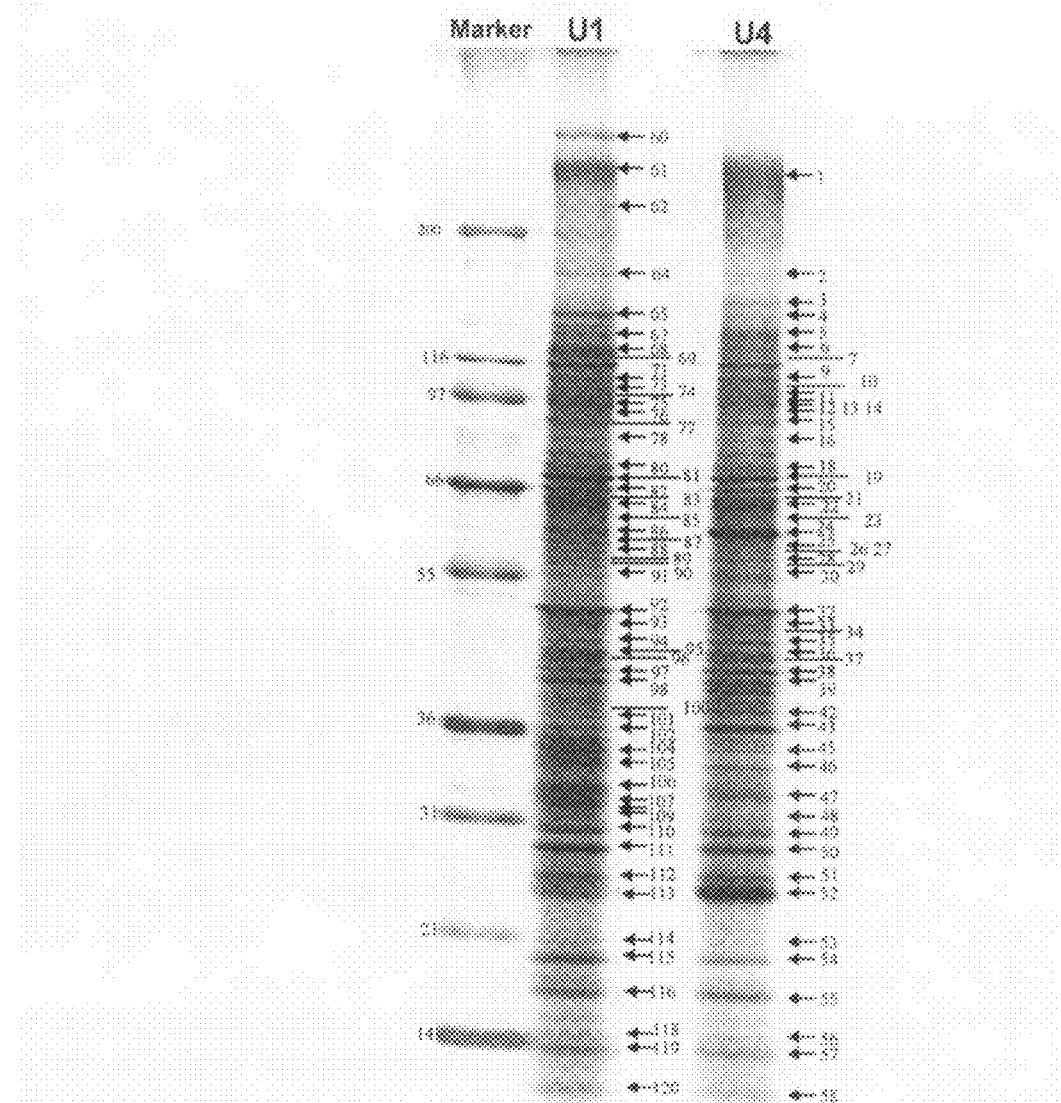
FIG. 1A and 1B are figures illustrating SDS-PAGE analysis of culture media harvested from U1 and U4 cells according to an embodiment of the present invention.

Reference will now be made in detail to the preferred embodiments of the present invention, examples of which are illustrated in the accompanying drawings. Wherever possible, the same reference numbers are used in the drawings and the description to refer to the same or like parts.

A detailed study was conducted to confirm the method of the present invention. The study included 33 bladder cancer patients treated with transurethral resection of bladder tumor between April 2004 and July 2005. Seventeen normal non-cancer subjects that consisted of 8 patients with urinary tract infection and 9 healthy donors were also included in this period of survey. Studies were undertaken with the approval by the institutional review board for the Protection of Human Subjects. All tumors were reviewed by an experienced genitourinary pathologist for the determination of the transitional cell carcinoma (TCC) of bladder. Pathological staging was performed according to the 2002 TNM staging and the World Health Organization (WHO) consensus classification for grading of these tumors.

MGH-U1 was established from a bladder tumor. MGH-U4 cell line was derived from a male who had a bladder tumor of carcinoma in situ and severe atypia of the bladder. U1 or U4 cells were grown in RPMI 1640 medium supplemented with 10% fetal bovine serum, 50 units/ml penicillin and 50 μg/ml streptomycin in a 5% $CO_2$ humidified incubator at 37° C.

The expression vector pcDNA3.1-H-RasS17N (DN-Ras) was from UMR cDNA Resource Center and the control vector pcDNA3.1 was the plasmid that H-Ras S17N cDNA had been excluded. Transfections were performed using Lipofectamine Reagent method. For establishment of stable clones, the DN-Ras or pcDNA3.1 vector transfected cells were distributed in 10-cm dishes at a number of $5 \times 10^5$ and 0.5 mg/ml of G418 was added to the cell culture at 48 hours after transfection. After selection with G418 for 3 weeks, individual clones were expanded to mass cultures and subsequently assayed for loss of Ras downstream ERK kinase activity. The transfectants were maintained in culture medium supplemented with 0.5 mg/ml of G418.

To obtain culture supernatants, cancer cells were grown to confluency in 15-cm tissue culture dishes. The cells were washed with serum-free medium and incubated in serum-free medium for 24 hours. The supernatants were then harvested and centrifuged to eliminate intact cells. The samples were dialyzed against water (molecular mass cutoff 3,500 Da) for 48 hours and concentrated by SpeedVac™. Protein concentrations of samples were determined using a BCA protein assay reagent.

One-dimensional SDS-PAGE was performed in a 16×18-cm 8-15% gels running at 140 V for 4 hours. Separated protein bands in the SDS-PAGE gel were visualized with Silver stain or Coomassie Blue stain.

Silver stained bands were excised and in-gel digested with trypsin according to procedures described previously. Briefly, the gels were destained by 1% potassium ferricyanide and 1.6% sodium thiosulfate. Then the proteins were reduced with 25 mM $NH_4HCO_3$ containing 10 mM dithiothreitol at 60° C. for 30 min and alkylated with 55 mM iodoacetamide at room temperature for 30 min. After reduction and alkylation, the proteins were digested with trypsin (20μg/ml) at 37° C. overnight. After digestion, the tryptic peptides were acidified with 0.5% trifluoracetic acid and loaded onto an MTP AnchorChip™ 600/384 TF. MALDI-TOF mass spectrometry analysis was performed on an Ultraflex™ MALDI-TOF mass spectrometer. Monoisotopic peptide masses were assigned and used for database searches with the MASCOT search engine.

The 50 ml of midstream void urine samples were collected from healthy donors and bladder cancer patients. Healthy donors and cancer patients had fasted at least 6 hours before samples were taken. To remove the insoluble materials and red blood cells (RBC), the samples were immediately centrifuged at 3000 rpm for 15 minutes at 4° C. The RBC was noted in the pellets. The supernatants that were clear of RBC were collected. They were then centrifuged at 15,000g for 30 minutes at 4° C. The final supernatants were then loaded onto centricon 5 kDa membrane for concentration of the proteins and removal of small interference molecules. Briefly, the centrions were spun at 3700g at 4° C. for 1 hour to reduce volumes to 1 ml. Two volumes of cold 20% TCA were added to the concentrated urine samples. The mixture was stored in ice for 30 minutes and pellet was obtained by centrifugation at 13,000 g for 20 minutes at 4° C. The pellet was washed twice with cold acetone. The protein amounts in urine concentrates were measured using the BCA protein assay and frozen at −80° C.

"Cells were lysed in RIPA buffer (1% Triton X-100, 1% SDS, 20 mM $Na_2HPO_4$,100 mM NaCl, 0.2 mM PMSF). Lysates were boiled in SDS sample buffer [62.5 mM Tris (pH 6.8), 5% β-mercaptoethanol (Merck), 10% glycerol, 2% SDS, 0.001% bromophenol blue], and was subsequently fractionated by 10% SDS-PAGE. Separated proteins in SDS-PAGE were electrotransferred to HYBOND™ -PVDF membrane. The PVDF membrane was then soaked in a blocking solution containing 5% (w/v) non-fat milk in TBST [20 mM Tris, pH 7.5, 0.5 M NaCl, 0.1% (v/v) Tween-20] for 1 hour at room temperature."

To assess the u-PA components levels, the soaked PVDF membrane was incubated with polyclonal Ab against pro-u-PA [diluted 1:1000 in 5% (w/v) non-fat milk in TBST] for 4 hours at room temperature, and washed with TBST three times for 15 minutes each and subsequently incubated in horse-radish peroxidase-conjugated goat anti-mouse IgG antibody (diluted 1:5000 in TBST buffer) at room temperature for 1 hour. After wash, immunobands were detected by the enhanced chemiluminescence reaction.

The Pearson chi-square or Fisher's extract test for trend was used to evaluate the trend between different tumor staging and tumor grading. Statistically significance was set at $p \leq 0.05$.

To search for potential biomarkers of bladder carcinoma, proteins secreted from two bladder cancer cell lines were systematically analyzed. The high malignant U1 and pre-malignant U4 cells were grown in serum-free medium for 24 hours and the culture supernatants were harvested. After concentration, proteins were resolved on 8-15% SDS-PAGE and silver-stained.

Figure 1B:
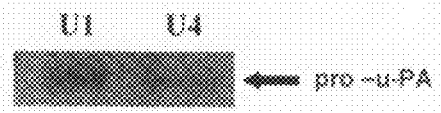

Refer to FIGS. 1A and 1B, which are figures illustrating SDS-PAGE analysis of culture media harvested from U1 and U4 cells according to an embodiment of the present invention; to FIG. 1C, which is a table illustrating bladder cancer cell line-secreted protein identified by MALDI TOF MS according to an embodiment of the present invention; and to FIG. 1D, which is a table illustrating Bladder cancer cell line-secreted proteins known to be highly-expressed or deregulated in other types of cancer according to an embodiment of the present invention.

U1 and U4 cells were grown in serum-free media for 24 hours and the culture supernatants from both cell lines were collected and processed. In FIG. 1A, fifteen micrograms of proteins were resolved on 8-15% gradient SDS-PAGE and then silver-stained. Protein bands detected in the supernatant fraction were marked, numbered and excised for further analysis. In FIG. 1B, fifteen micrograms of proteins from the cultured media of U1 and U4 cells were separated by SDS-PAGE, transferred onto PVDF membrane, and then probed with specific antibodies against the pro-u-PA.

The bands, which are numbered in FIG. 1A, were excised individually, in-gel digested with trypsin, and identified by MALDI-TOF mass spectrometry. Forty-nine U1-secreted proteins were identified while 47 proteins were identified for U4 cells. Among them, 46 proteins were identified in both cell lines as shown in FIG. 1C. Laminin alpha-5 chain, ADP-ribosylation factor guanine nucleotide-exchange factor 2, and glyceraldeyde-3-phosphate dehydrogenase were only identified in U1 cells while alpha 3b subunit of laminin 5 was identified in U4 cells only. Expression of 17 of the identified proteins has been reported to be deregulated in certain types of tumor as shown in FIG. 1D.

An important and apparently causal role for urokinase-type plasminogen activator (u-PA) system in cancer progression and metastasis has been suggested. To verify the mass spectrometry-assisted identification of pro-u-plasminogen activator (pro-u-PA), proteins in cultured media of U1 and U4 cells were subjected to Western blot analysis. The results showed that pro-u-PA ($M_r$ 56 kDa) were both detected in U1 and U4 cells as shown in FIG. 1B.

Figure 2A:
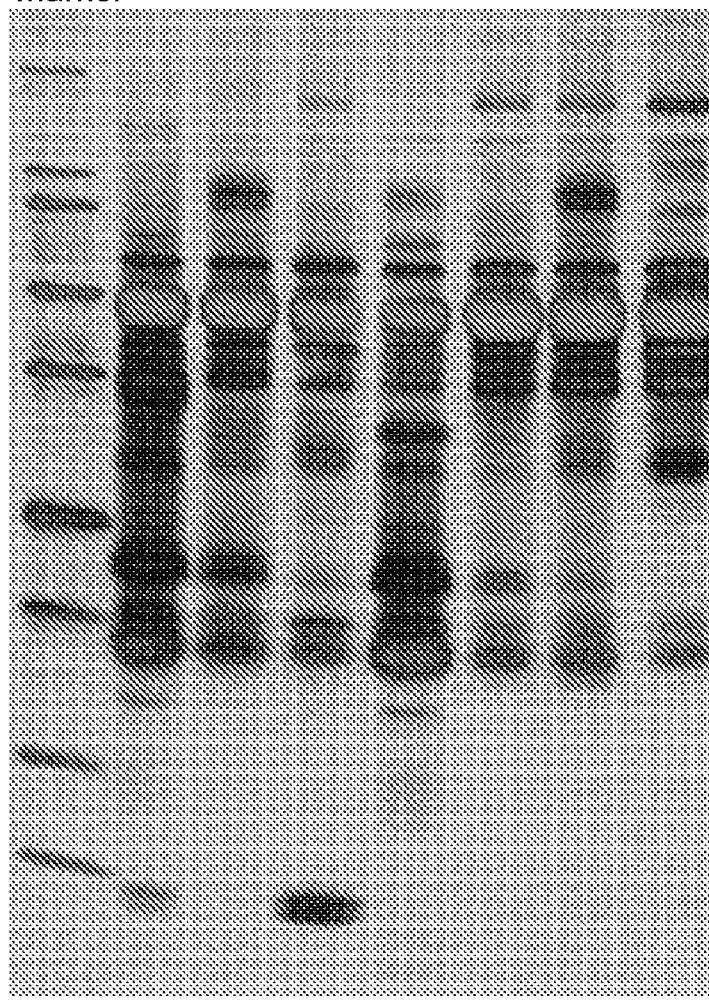
FIGS. 2A and 2B are figures illustrating Western blot analysis of pro-u-PA in urine samples from cancer patients and normal controls according to an embodiment of the present invention.
Figure 2B:
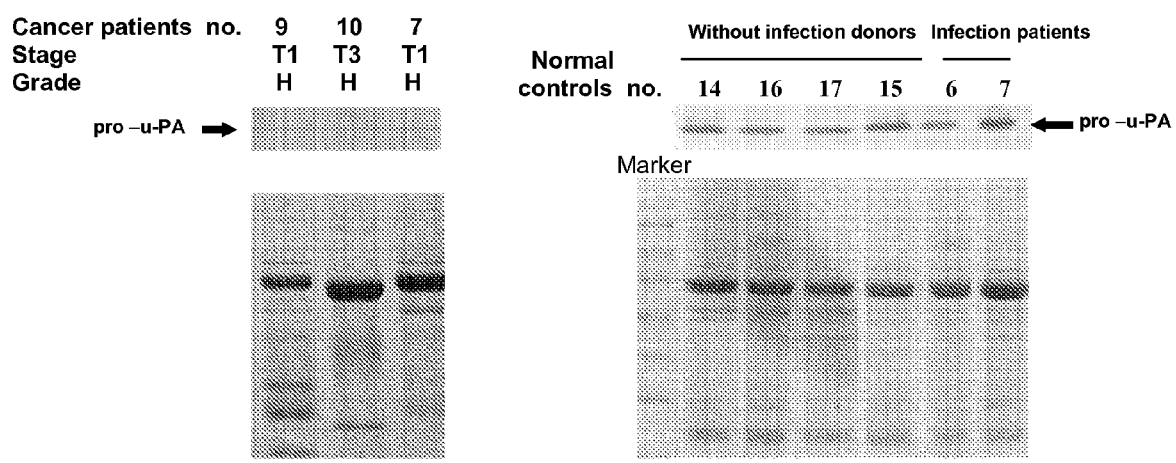

Refer to FIGS. 2A and 2B, which are figures illustrating Western blot analysis of pro-u-PA in urine samples from cancer patients and normal controls according to an embodiment of the present invention and to FIG. 2C which is a table illustrating background and clinical characteristics of 50 cases stratified by urine analysis according to an embodiment of the present invention.

In FIG. 2A, fifteen micrograms of urine protein samples from the cancer patients were resolved on 8-15% gradient SDS-PAGE and silver-stained (lower panel) or blotted onto PVDF membrane, and then probed with specific antibodies against pro-u-PA (upper panel). In FIG. 2B, fifteen micrograms of urine protein samples from the cancer patients and normal control persons were separated by 10% SDS-PAGE stained with Coomassie Blue (lower panels), or blotted onto PVDF membrane, and then probed with specific antibodies against pro-u-PA (upper panel).

To correlate the urinary levels of pro-u-PA with clinical significance, the urine samples from bladder cancer patients and normal controls for expression of pro-u-PA were examined. Pro-u-PA was abundant in the control samples. Although pro-u-PA was also detected in 17 of 33 cancer samples, most of the positive specimens (16/17, 94%) were of the early stage T1 or Ta. On the other hand, 8 of 16 (50%) cancer urine samples in which no pro-u-PA protein could be detected were from patients of tumor stages T2 or higher. Moreover, 13 of 16 (81%) of these pro-u-PA-negative urine samples were from patients of high grades. In contrast, of the 17 pro-u-PA-positive cancer samples, 12 (71%) were from patients of lower grades. A statistically significant relationship was thus established between the low or absent level of pro-u-PA in urines with high stages and grades. The loss of pro-u-PA for diagnosis of more advanced bladder carcinoma had 72.2% sensitivity and 90.6% specificity.

Figure 3A:
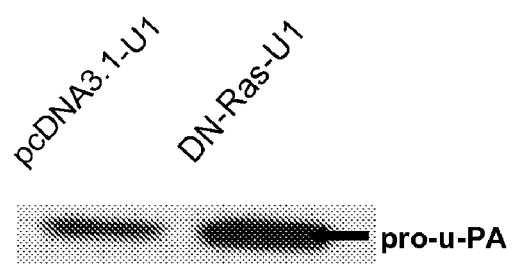
FIGS. 3A and 3B are figures illustrating analysis of the cultured media harvested from U1 cells stably-expressing vector or a dominant negative form of Ras according to an embodiment of the present invention.
Figure 3B:
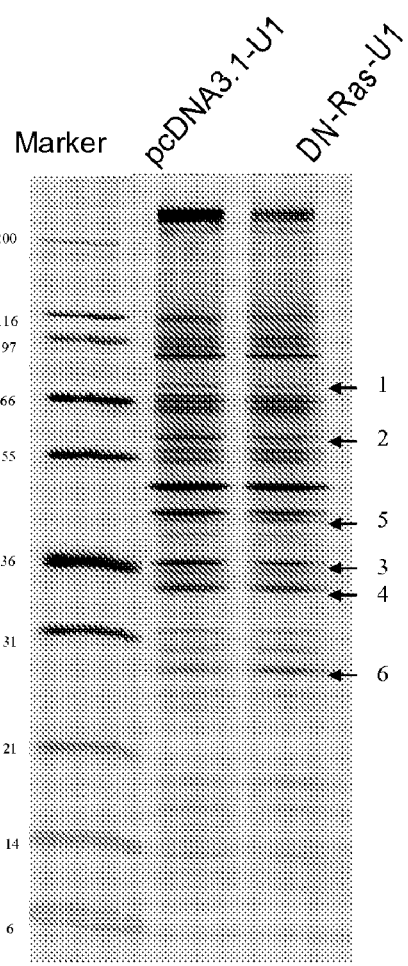

Refer to FIGS. 3A and 3B, which are figures illustrating analysis of the cultured media harvested from U1 cells stably-expressing vector or a dominant negative form of Ras according to an embodiment of the present invention and to FIG. 3C, which is a table illustrating differential protein expression profiles of pcDNA3.1-U1 & DN-Ras-U1 cells according to an embodiment of the present invention.

In FIG. 3A, fifteen micrograms of proteins from the cultured media of U1 cell lines stably harboring vector (pcDNA3.1-U1) or a dominant negative form of Ras (DN-Ras-U1) were separated by SDS-PAGE, transferred onto PVDF membrane, and then probed with specific antibodies against the indicated target proteins. In FIG. 3B, protein expression profiles, as shown on silver-stained gel, of the cultured media (15 µg) from pcDNA3.1-U1 and DN-Ras-U1 cell lines. Protein bands that exhibited significantly different levels between these two cell lines were marked, numbered and excised for further analysis.

Ras signalling pathway is linked directly to growth stimulation. Activation of Ras triggers uncontrolled proliferation and morphological alteration, contributing to the malignant phenotype of cancer cells. To further determine whether the u-PA system is associated with oncogenic activation by Ras, the study's approach was to constitutively express Ras dominant-negative protein in U1 cells and look for any changes in pro-u-PA level in cultured media. The results showed that constitutive expression of Ras dominant-negative protein led to increased pro-u-PA detection in cultured media as shown in FIG. 3A. Proteins from the culture media were also resolved on 8-15% SDS-PAGE and silver-stained as shown in FIG. 3B. The secreted proteins that were expressed at significantly different levels in the cultured media from U1 and DN-Ras U1 cells were identified by MALDI-TOF mass spectrometry as shown in FIG. 3C. Relatively lower levels of heat shock protein 70, M2-type pyrurate kinase, glyceraldehydes-3-phosphate dehydrogenase and lactate dehydrogenase but higher levels of phosphoglycerate kinase 1 and triosephosphate isomerase 1 were detected in the cultured media from DN-Ras U1 cells as compared to vector-transfected U1 cells.

U4 cell line was derived from a bladder biopsy specimen diagnosed as severe atypia of the urothelium. U4 cells can grow in culture, but fail to produce tumor in nude mice and could not form colonies in soft agar. Based on the characterizations including growth, morphology, colony formation and tumorigenicity in nude mice, U1 cells represent cells with high degree of malignancy, while U4 cells are considered to be pre-malignant.

Proteins secreted from tumor cells are potential biomarkers for disease diagnosis and/or prognosis. In the study, a set of proteins (>47) secreted from bladder carcinoma was systematically identified by a straightforward proteomic approach, consisting of SDS-PAGE and MALDI-TOF mass spectrometry. The expression profiles of the secreted proteins in U1 and U4 cells were similar, but not identical. Out of 50 proteins, 46 appeared in the cultured medium from both cell lines, whereas only 4 were unique to the individual cell line. Furthermore, seventeen proteins secreted from bladder cancer cells are reported as highly expressed or deregulated in other types of cancers. Future studies targeted at all these proteins will help to establish a complete panel of potential diagnostic biomarkers. Additionally, the systematic approach reported herein is a valid method for the large-scale identification of multiple tumor markers. 85% of superficial tumors recur, of which 10% to 15% progress to muscle invasive cancer. Thus, the treatment of bladder transitional cell carcinoma is dictated by several factors. The most clinically significant prognostic parameters for tumor recurrence and invasion of bladder cancer are grade, stage, lymphatic invasion, tumor size, carcinoma in situ, multifocality and the rate of tumor recurrence. Of these parameters, pathological stage and tumor grade are most important and relevant. However, staging errors are unavoidable, occurring usually in cases of high and intermediate stage diseases, of which approximately 33% are under- and 10% are over-staged.

An ideal prognostic factor must be reliable, so direct and sound treatment decisions can be made on individuals. Cystoscopy along with cytology is the mainstay for diagnosing bladder cancer. Cytology is specific for diagnosis of bladder carcinoma but less sensitive particularly in detecting low-grade disease. Cystoscopy on the other hand is invasive and a relatively costly technique and may also be inconclusive at times particularly in case of cystitis. A simple non-invasive marker for detecting bladder cancer would thus be very beneficial. Pro-u-PA identified in the study is differentially expressed in urines of bladder cancer patients as compared to normal controls. Pro-u-PA is detected in all of the urine samples from the normal and in 17 of the cancer samples, most of which are at early stage or low grade. A statistically significant relationship was found between the low level and absence of pro-u-PA signals in urines with high tumor stages and grades of the samples. Low level of urine pro-u-PA is associated with high tumor grading and staging, which in turn indicates poor prognosis for bladder carcinoma. Constitutive expression of Ras dominant-negative protein results in the increased pro-u-PA expression in cultured media. Considering that Ras is functionally implicated in tumor progression in many types of malignant cells, the loss of pro-u-PA in cultured media or in urine signals oncogenic transformation. The pro-u-PA thus represents an important potential urine protein marker for bladder carcinoma. The data herein presented serves as evidence that pro-u-PA can be secreted and detected in normal urine samples whereas it may be converted to another product and thus not secreted/detected in urine from cancer patients. Furthermore, in the cultured media derived from DN-Ras U1 cells as compared to vector-transfected U1 cells, lower levels of heat shock protein 70, M2-type pyrurate kinase, glyceraldehydes-3-phosphate dehydrogenase and lactate dehydrogenase but higher levels of phosphoglycerate kinase 1 and triosephosphate isomerase 1 are detected. These proteins represent another set of protein markers that are directly related to Ras oncogenic function.

Extracellular proteolytic enzymes have been implicated in cancer metastasis. The release of proteolytic enzymes in tumors facilitates cancer-cell invasion into surrounding normal tissue by breakdown of basement membranes and ECM [14]. Plasminogen activation can play an important role in this process. The plasminogen activator u-PA is capable of catalyzing the conversion of the inactive zymogen plasminogen to the active proteinase plasmin, which can then degrade most extracellular proteins. Studies have established that the level of u-PA in malignant tumors is significantly higher than in the corresponding normal tissue or in benign tumors of the same tissue. u-PA was the first proteinase shown to be a prognostic marker in human malignancy. It has been shown that patients with breast tumors containing high levels of u-PA enzyme activity have a significantly shorter disease-free interval than patients with tumors containing low levels of activity. Higher u-PA antigen levels were subsequently found to be in correlation with a shortened overall survival in this disease. U-PA-antigen levels appear to be among the most relevant and direct strongest prognostic factors for breast cancer. Apart from breast cancer, u-PA has also been shown to be a prognostic marker in other malignancies, including cancers of lung and bladder, stomach, ovary and brain. In the study, u-PA is virtually not detected in the normal urine or minimally present in the few cancer urine samples. Such low level of expression suggests that pro-u-PA are more readily converted to u-PA in cancer cells that consequently results in the loss of pro-u-PA in cancer urines. Therefore, loss of pro-u-PA rather than low detection of u-PA in urines serves as a more reliable cancer biomarker.

The large-scale identification of secreted proteomes developed herein serve as an ideal and efficient method in the establishment of a panel of potential biomarkers. Due to low sensitivity of the combination of 1-D gel electrophoresis and MALDI-TOF-MS, some potential markers with low expression may be overlooked. However, since such analysis of the secreted protein can be done with little interference of cell-host microenvironment, the method of the present invention is an efficient means for identifying important cancer biomarkers. Furthermore, the non-invasive detection for biomarkers in urine is useful for clinical application in diagnosis and prognosis of bladder cancers. Proteins secreted from bladder tumor or normal cells and present in urine are of diagnostic or prognostic value; the biomarkers identified in the study of the present invention provide therapeutic targets for the future development of novel anti-tumor agents.

Therefore, the present invention provides an efficient method using pro-u-PA as a novel clinical tool to identify progression of bladder cancer.

It will be apparent to those skilled in the art that various modifications and variations can be made to the present invention without departing from the scope or spirit of the invention. In view of the foregoing, it is intended that the present invention cover modifications and variations of this invention provided they fall within the scope of the invention and its equivalent.

What is claimed is:

1. A method of identifying progress of cancer comprising:
    obtaining a 50 ml urine sample from a person who has fasted for at least six hours:
    removing insoluble materials and red blood cells from the urine by centrifuging the urine at 3000 rpm for 15 minutes at 4° C., and producing first supernatants;
    centrifuging the first supernatants at 15,000 g for 30 minutes at 4° C. to produce second supernatants;

loading the second supernatants onto a membrane in a centrifuging filter device;

producing concentrated proteins and removing interference molecules by operating the centrifuging filter device to spin at 3700 g at 4° C. for 1 hour by which concentrated urine is produced by the operation reducing volume of the second supernatants to 1 ml;

adding two volumes of cold 20% TCA to the concentrated urine to produce an intermediate mixture;

storing the intermediate mixture in ice for thirty (30) minutes;

centrifuging the iced intermediate mixture at 13,000 g for 20 minutes at 4° C. to obtain pellets;

washing the pellets twice with cold acetone;

resolving protein in the urine on 8-15% gradient SDS-PAGE and silver staining or blotting onto PVDF membrane;

determining a level of the pro-u-plasminogen activator present in the urine; and determining a loss or absence of pro-u-plasminogen activator in the urine.

2. The method of identifying cancer progress of claim 1, the cancer comprising bladder cancer.

3. The method of identifying cancer progress of claim 1, where a loss or absence of pro-u-plasminogen activator indicates the cancer is high stage, high grade, or both.

4. A method of identifying cancer progress comprising:

obtaining a 50 ml urine sample from a person who has fasted for at least six hours;

removing insoluble materials and red blood cells from the urine by centrifuging the urine at 3000 rpm for 15 minutes at 4° C., and producing first supernatants;

centrifuging the first supernatants at 15,000g for 30 minutes at 4° C. to produce second supernatants;

loading the second supernatants onto a membrane in a centrifuging filter device;

producing concentrated proteins and removing interference molecules by operating the centrifuging filter device to spin at 3700 g at 4° C. for 1 hour by which concentrated urine is produced by the operation reducing volume of the second supernatants to 1 ml;

adding two volumes of cold 20% TCA to the concentrated urine to produce an intermediate mixture;

storing the intermediate mixture in ice for thirty (30) minutes;

centrifuging the iced intermediate mixture at 13,000 g for 20 minutes at 4° C. to obtain pellets;

washing the pellets twice with cold acetone;

resolving protein in the urine on 8-15% gradient SDS-PAGE and silver staining or blotting onto PVDF membrane;

determining a level of pro-u-plasminogen activator present in the urine; and using the level of pro-u-plasminogen activator as a tool to identify progression of the cancer.

5. The method of identifying cancer progress of claim 4, the cancer comprising bladder cancer.

6. The method of identifying cancer progress of claim 4, where a loss or absence of pro-u-plasminogen activator identifies cancer progress.

7. The method of identifying cancer progress of claim 4, where a loss or absence of pro-u-plasminogen activator indicates the cancer is high stage, high grade, or both.

\* \* \* \* \*